United States Patent
Leigh

(10) Patent No.: US 8,219,361 B2
(45) Date of Patent: Jul. 10, 2012

(54) VIBRATION ANALYSIS

(76) Inventor: Nigel Leigh, Christchurch (NZ)

( * ) Notice: Subject to any disclaimer, the term of this patent is extended or adjusted under 35 U.S.C. 154(b) by 0 days.

(21) Appl. No.: 12/891,757

(22) Filed: Sep. 27, 2010

(65) Prior Publication Data

US 2011/0015899 A1 Jan. 20, 2011

Related U.S. Application Data

(63) Continuation of application No. 11/305,420, filed on Dec. 16, 2005, now Pat. No. 7,805,281.

(30) Foreign Application Priority Data

Dec. 16, 2004 (NZ) .......................................... 537244

(51) Int. Cl.
*H03F 1/26* (2006.01)
*H04B 15/00* (2006.01)
(52) U.S. Cl. ......... 702/189; 702/190; 702/191; 702/197
(58) Field of Classification Search ..................... 702/54, 702/66, 67, 69–77, 189–197
See application file for complete search history.

(56) References Cited

U.S. PATENT DOCUMENTS

| | | | |
|---|---|---|---|
| 5,477,730 A * | 12/1995 | Carter | 73/609 |
| 6,275,781 B1 * | 8/2001 | Maness et al. | 702/182 |
| 6,763,312 B1 | 7/2004 | Judd | |

OTHER PUBLICATIONS

Duncan L. Carter, A New Method of Processing Rolling Element Bearing Signals, 5 pages.

* cited by examiner

*Primary Examiner* — Phuong Huynh
(74) *Attorney, Agent, or Firm* — Pitts & Lake, P.C.

(57) ABSTRACT

The present invention relates to vibration analysis and in particular, but not limited to, the derivation of multiple types of vibration signals from one vibration signal for vibration analysis. In the preferred method of the invention the vibrations of an object are measured using at least one vibration sensor, wherein the vibration sensor converts vibrations into an electrical vibration signal. The electrical vibration signal is digitized based on a first frequency, wherein the first frequency is selected from a plurality of possible frequency values. A first type of vibration signal is derived from the digitized vibration signal. A second type of vibration signal is then derived from the digitized vibration signal based on a second frequency. The second frequency is rationally determined from, and lower than, the value selected for the first frequency. The invention also provides apparatus for deriving multiple types of vibration signals from one measured vibration signal for vibration analysis.

20 Claims, 1 Drawing Sheet

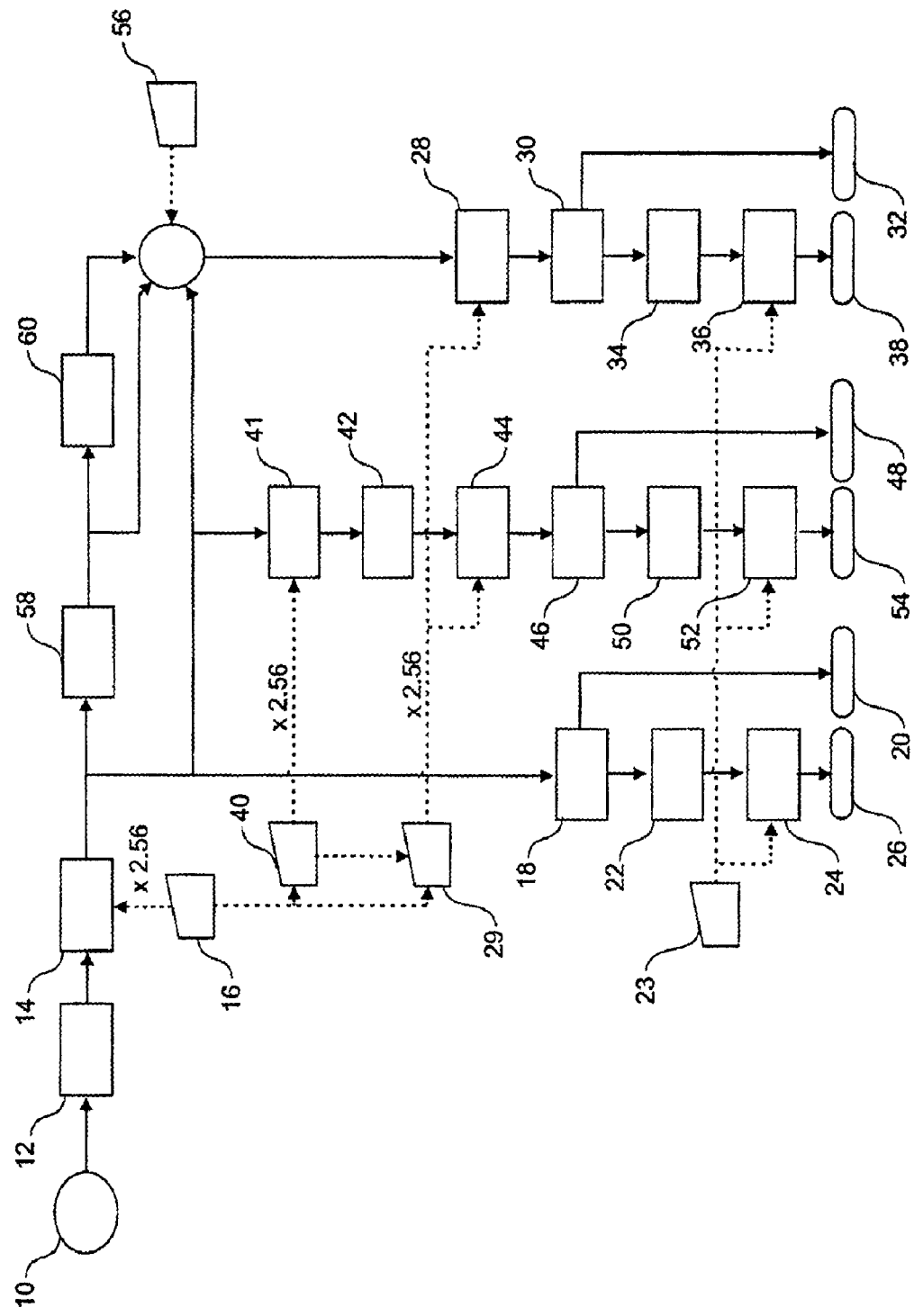

VIBRATION ANALYSIS

CROSS-REFERENCE TO RELATED APPLICATIONS

This application is a continuation of U.S. application Ser. No. 11/305,420, filed Dec. 16, 2005, now U.S. Pat. No. 7,805,281 which claims the benefit of New Zealand Patent Application No. 537244, filed Dec. 16, 2004, which is hereby incorporated by reference.

FIELD OF THE INVENTION

The present invention relates to vibration analysis and in particular, but not limited to, the derivation of multiple types of vibration signals from one vibration signal for vibration analysis.

BACKGROUND OF THE INVENTION

Vibration analysis is commonly used in the art of fault-detection in machines. Prior to the emergence of this analysis, faults within machines were difficult to detect before mechanical damage occurred. Such faults often led to costly machine downtimes and costly servicing due to extensive mechanical damage. However, by detecting and analyzing vibrations produced by a machine, certain symptoms of impending fault or failure can be detected before major mechanical damage occurs.

The first step in vibration analysis is to gather and record vibration data. The data is then analyzed according to known analytical techniques. In recent times, a plurality of analytical techniques has been discovered. Most of these techniques have required separate recordings of vibration data to be made at each measurement location. When this is done on an industrial scale for a large number of machines, the data collection step can become costly simply due to the time involved in the collection. For example, on a large site with 500 machines, each being monitored in the horizontal and vertical directions at each of four points, with three types of measurements being taken at each of these measurement locations, a total of 12,000 recordings must be taken.

The time it takes to acquire each recording depends upon the specific parameters selected. These include, for example, the recording type, the highest frequency of interest or $F_{max}$, and the number of spectral lines. Given these selections, the recording time is governed by relevant physics/signal processing principals. Values of a few seconds are typical. When combined with the time required to walk between all of the measurement locations, to attach the sensor and to wait for it to settle, the collection process can become very time-consuming.

There have been attempts in prior art to address the time-consuming factor of data collection and analysis. U.S. Pat. No. 5,943,634 to Piety, et al., describes a data collection, analysis and storage system that minimizes data collection time by parameterizing time-domain vibration waveforms. Instead of recording data continuously, Piety teaches a technique of recording parameters that could characterize the time-waveform, such as Maximum Peak and Maximum Peak-to-Peak. Time and storage space is made efficient since continuous recording is only performed when the analyzed parameters are in alarm.

The main disadvantage of this system is that the resolution and extent of valuable data collected is reduced as a consequence of saving time and space. It is acknowledged in the description of the patent that time data is a "highly useful data to assist in the interpretation of certain classes of problems commonly experienced in industry." However, since "saving all of the time data . . . is simply too burdensome to be considered a realistic option," Piety employs reduced-volume data collection by monitoring key parameters of the time data.

In another U.S. patent to Piety, et al., namely U.S. Pat. No. 5,965,819, the time-consuming factor in analyzing vibration signals is somewhat addressed. In particular, Piety, et al., employs a parallel processing system to simultaneously perform multiple measurements on the detected vibration signal obtained from a single vibration sensor. This setup results in processing that is independent from chain to chain.

It is noted however that the independence of the parallel processing chains comes at a cost—the necessity for each chain to have a complete processing ability results in an increased cost of the device. For each chain, for example, there is a requirement for an analog-to-digital converter. If three separate analyzes are to be performed, the device will require three analog-to-digital converters.

It is an object of the present invention to provide a method and apparatus which addresses at least one of the abovementioned limitations and/or which at least provides the public with a useful choice.

SUMMARY OF THE INVENTION

In one aspect, the invention broadly comprises a method of deriving multiple types of vibration signals from one vibration signal for vibration analysis comprising the steps of:
  measuring the vibrations of an object using at least one vibration sensor, wherein the vibration sensor converts vibrations into an electrical vibration signal;
  digitizing the electrical vibration signal based on a first frequency, wherein the first frequency is selected from a plurality of possible frequency values;
  deriving a first type of vibration signal from the digitized vibration signal; and
  deriving a second type of vibration signal from the digitized vibration signal based on a second frequency, wherein the second frequency is rationally determined from and lower than the value selected for the first frequency.

Preferably, the method of the invention further comprises the step of deriving a third type of vibration signal from the digitized vibration signal based on the second frequency and a third frequency, wherein the third frequency is rationally determined from and lower than the value selected for the first frequency.

The first frequency is preferably an upper cut-off frequency and the first type of vibration signal is preferably a high frequency waveform of the digitized vibration signal. Also, the second frequency is preferably a lower cut-off frequency and the second type of vibration signal is preferably a low frequency waveform of the digitized vibration signal. The third frequency is preferably a demodulation cut-off frequency and the third type of vibration signal is preferably a demodulation waveform of the digitized vibration signal.

The step of deriving a first type of vibration signal from the digitized vibration signal preferably further comprises the steps of buffering the digital vibration signal and emptying the contents of the buffer as the high frequency waveform of the digitized vibration signal.

The step of deriving a second type of vibration signal from the digitized vibration signal based on a second frequency preferably further comprises the steps of: reducing the frequency of the digital vibration signal to at least approximate the lower cut-off frequency using at least one decimation filter; buffering the filtered vibration signal and emptying the contents of the buffer as the low frequency waveform of the digitized vibration signal.

The step of deriving a third type of vibration signal from the digitized vibration signal based on the second frequency and the third frequency preferably further comprises the steps of: high-pass filtering the digital vibration signal at the demodulation cut-off frequency to produce a filtered signal; detecting the envelope of the filtered signal to produce an envelope signal; reducing the frequency of the envelope signal to at least approximate a frequency rationally determinable from and lower than the first frequency using at least one decimation filter; buffering the reduced-frequency envelope signal and emptying the contents of the buffer as the demodulation waveform of the digitized vibration signal.

Preferably, the step of reducing the frequency of the envelope signal to a frequency rationally determinable from and lower than the first frequency comprises reducing the frequency of the envelope signal to at least approximate the lower cut-off frequency.

The step of deriving a third type of vibration signal from the digitized vibration signal based on the second frequency and the third frequency may also further comprise the steps of: high-pass filtering the digital vibration signal at the demodulation cut-off frequency to produce a filtered signal; detecting the envelope of the filtered signal to produce an envelope signal with a frequency rationally determinable from and lower than the first frequency; buffering the envelope signal; and emptying the contents of the buffer as the demodulation waveform of the digitized vibration signal.

Preferably, further processing is performed on the contents of the buffer to produce a frequency-domain signal, where the further processing comprising the steps of: windowing the contents of the buffer; transforming the windowed buffer contents into a frequency spectrum; and determining the averaged frequency spectrum. Preferably, the vibration sensor is an accelerometer and the digitized vibration signal is an acceleration vibration signal and wherein the method further comprises the steps of: integrating the acceleration vibration signal to obtain a velocity vibration signal; integrating the velocity vibration signal to obtain a displacement vibration signal; selecting one of either the acceleration, velocity or displacement vibration signal; and deriving multiple types of vibration signals from the selected vibration signal according to the methods previously described.

In a further aspect, the invention broadly comprises an apparatus for deriving multiple types of vibration signals from one measured vibration signal for vibration analysis comprising: at least one vibration sensor for measuring the vibrations of an object by converting the vibrations into an electrical vibration signal; an analog-to-digital converter to convert the electrical vibration signal to a digital vibration signal, wherein the analog-to-digital converter has a sampling rate based on a value selected from a plurality of possible values for a first frequency; and at least one signal processor for deriving a first type of vibration signal from the digital vibration signal and for deriving a second type of vibration signal from the digital vibration signal based on a value rationally determined from and lower than the selected value of the first frequency. Preferably, the signal processor also derives a third type of vibration signal from the digital vibration signal based on the second frequency and a third frequency, wherein the third frequency is selected from values rationally determined from and lower than the value selected for the first frequency.

The first frequency is preferably an upper cut-off frequency and first type of vibration signal is preferably a high frequency waveform of the digital vibration signal. Also, the second frequency is preferably a lower cut-off frequency and second type of vibration signal is preferably a low frequency waveform of the digital vibration signal. The third frequency is preferably a demodulation cut-off frequency and third type of vibration signal is preferably a demodulation waveform of the digital vibration signal. Preferably, the signal processor includes a waveform buffer to buffer the digital vibration signal, and wherein the signal processor outputs the contents of the buffer as the high frequency waveform of the digital vibration signal.

Preferably, the signal processor includes at least one decimation or sub-sampling filter to reduce the frequency of the digital vibration signal to at least approximate the lower cut-off frequency; and a waveform buffer to buffer the filtered vibration signal; wherein the signal processor outputs the contents of the buffer as the low frequency waveform of the digital vibration signal.

Preferably, the signal processor includes: a high-pass filter having a cut-off frequency at the demodulation cut-off frequency to produce a filtered signal; an envelope detector to generate an envelope signal from the filtered signal; at least one decimation or sub-sampling filter to reduce the frequency of the envelope signal to at least approximate a frequency rationally determinable from and lower than the first frequency; and a waveform buffer to buffer the filtered envelope signal; wherein the signal processor outputs the contents of the buffer as the demodulated waveform of the digital vibration signal.

Preferably, the decimation or sub-sampling filter reduces the frequency of the envelope signal to at least approximate the lower cut-off frequency.

Preferably, the signal processor includes: a high-pass filter having a cut-off frequency at the demodulation cut-off frequency to produce a filtered signal; an envelope detector to generate an envelope signal from the filtered signal, where the frequency of the envelope signal at least approximates a frequency rationally determinable from and lower than the first frequency; and a waveform buffer to buffer the filtered envelope signal; wherein the signal processor outputs the contents of the buffer as the demodulated waveform of the digital vibration signal.

Preferably, the signal processor converts the contents of the buffer into a frequency domain signal, the signal processor further comprising: a windowing means to window the contents of the buffer; a transforming means to obtain the frequency spectrum of the windowed buffer contents; and an averaging means to determine the averaged frequency spectrum.

Preferably, the vibration sensor is an accelerometer and the digital vibration signal is an acceleration vibration signal and wherein the apparatus further comprises: at least one integrator to integrate the acceleration vibration signal to obtain the velocity vibration signal; at least one integrator to integrate the velocity vibration signal to obtain the displacement vibration signal; selecting means to allow selection of either the acceleration, velocity or displacement vibration signal, from which the multiple types of vibration signals will be derived.

The term "comprising" as used in this specification and claims means "consisting at least in part of," that is to say when interpreting statements in this specification and claims which include that term, the features, prefaced by that term in each statement, all need to be present but other features can also be present.

This invention may also be said broadly to consist in the parts, elements and features referred to or indicated in the specification of the application, individually or collectively, and any or all combinations of any two or more said parts, elements or features. Where specific integers are mentioned herein which have known equivalents in the art to which this invention relates, such known equivalents are deemed to be incorporated herein as if individually set forth.

BRIEF DESCRIPTION OF THE DRAWINGS

Preferred forms of the method of and apparatus of the invention will now be described with reference to the accompanying figure in which:

FIG. 1 is a flow diagram showing the embodiment where three types of vibration signals are derived from a measured and digitized vibration signal.

DETAILED DESCRIPTION

As used herein, the term "type" in reference to signals refers to the composition of frequencies in the signal. This includes, without limitation, high frequency signals comprising substantially only frequencies less than an upper cut-off frequency, low frequency signals comprising substantially only frequencies less than a lower cut-off frequency and demodulation signals comprising frequencies that have been demodulated in the manner hereinafter described.

As used herein, the term "electrical vibration signal" refers to a vibration signal expressed in electrical form. Such an electrical form is commonly obtained using a vibration sensor (such as an accelerometer) to convert the mechanical vibrations of an object into electrical signals that represent the mechanical vibrations. Electrical vibration signals may be saved in some form of electronic storage means, such as memory banks or disk storage devices. The saved electrical vibration signals may later be retrieved and processed according to the method of the present invention.

As used herein with reference to values, the term "rationally determined" refers to values derived from one or more other values by way of multiplication or division using rational numbers. A rational number is a ratio of two integers x and y, usually expressed as a fraction x/y. Thus, given a value of 100, rationally determined values include 10 (when divided by 10 or 10/1) or 60 (when multiplied by 0.6 or 3/5). This will be described in context later in the specification.

Referring to FIG. 1, the vibrations of an object, such as an industrial motor, is sensed using an accelerometer in step 10. The accelerometer converts mechanical vibration signals into electrical vibration signals that represent the mechanical vibrations. The electrical vibration signals that are created are then preferably conditioned in step 12. Depending on the application, the electrical vibration signals may undergo any one of, or a combination of: scaling, direct-current (DC) offset and anti-alias filtering. Persons skilled in the art will be familiar with these well-known practices and situations in which these practices are best employed.

The electrical vibration signal, which has preferably undergone conditioning, is then converted into digital form using an analog-to-digital converter or ADC in step 14. The sampling rate of the ADC in the present invention is governed by the selection of a first frequency in step 16.

By selecting a certain frequency in step 16, the ADC will create a digitized vibration signal that is a digital representation of the electrical vibration signal. In the preferred embodiment, the first frequency is an upper cut-off frequency. The selection of an upper cut-off frequency determines the highest frequency content in the digitized vibration signal. The upper cut-off frequency, or $F_{max(high)}$, is tied to the sampling rate in the ADC by the relationship shown in Equation (1):

$$\text{Sampling Rate (Hz)} = F_{max(high)} \times 2.56. \quad (1)$$

The value of 2.56 is typical in the industry and is chosen to satisfy normal Nyquist and filtering requirements. Once the sampling rate is calculated and implemented, frequencies above that of the chosen $F_{max(high)}$ will be essentially removed from the digitized vibration signal. Effectively then, the selection in step 16 is a low-pass filter cut-off selection.

In vibration analysis for most machines, $F_{max(high)}$ can be chosen from the following values in Hertz: 40,000; 20,000; 10,000; 8,000; 5,000; 4,000; 2,500; 1,250; and 1,000. It should be appreciated that this set of values is only one of a plethora of sets that could be employed. However, there is a clear relationship between the values in that the lower values are rationally determinable from the higher values. This relationship between values of $F_{max(high)}$ contributes to the reduced calculation for further values described hereinafter in greater detail.

It is noted, however, that given the advent of microprocessors with high processing powers, the requirement of such an efficient relationship between the $F_{max(high)}$ values can be circumvented. In those situations, the microprocessors will have to perform high level division and calculation for each of the more complex values of $F_{max(high)}$.

The digitized vibration signal produced in step 14 is then processed in the first branch of the flow diagram, in particular in the waveform buffer of step 18. As its name suggests, the waveform buffer buffers or accumulates the incoming digitized vibration signal to reconstruct a time waveform.

Once the buffer in step 18 reaches a predetermined capacity, the contents of the buffer are outputted as the first type of vibration signal in a time waveform in step 20. Typical buffer lengths are 1,024; 2,048; 4,096; and 8,192. These correspond to spectra which contain 400; 800; 1,600; and 3,200 spectral lines, respectively, based on a 2.56-relationship similar to that of Equation 1.

If the first frequency is an upper cut-off frequency, the first signal type outputted will consequently be a high frequency waveform. This waveform is a time waveform of the detected vibrations, where vibration frequencies higher than the $F_{max(high)}$ frequency have been filtered. Ideally, the time waveform is displayed so that a maintenance operator can selectively determine an appropriate $F_{max(high)}$ to use and discern the resulting waveform.

It is also desirable to determine the frequency spectrum of the digitized vibration signal. This is done by firstly windowing and performing, for example, a Fast Fourier Transform (FFT) on the contents of the buffer, as shown in step 22. Although the present invention will herein be described with reference to the FFT process, other processes that achieve the result of determining the frequency spectrum can also be employed, such as the Discrete Fourier Transform (DFT) and its variants for example.

The FFT process in step 22 is repeated several times on subsequent waveform buffers to produce multiple raw spectra. The raw spectra produced in the FFT process are then averaged together in step 24. The averaging process can be controlled by the user, shown as the selection in step 23. This selection controls the number of spectra that will be averaged together. The result of the averaging process in step 24 is a spectrum in which each spectral line has been calculated by averaging each of the matching spectral lines in the raw spectra.

Once processed in step 24, a frequency spectrum of the digitized signal is outputted in step 26. As with the time waveform, the frequency spectrum here will be the high frequency spectrum, which displays all frequencies in the digitized vibration signal that are under the value selected for $F_{max(high)}$.

The digitized vibration signal produced in step 14 is also sent to another processing branch, which effectively is a parallel processing branch to that of the first branch. In this processing branch, the digitized signal firstly undergoes a decimation process in step 28. Decimation, or sub-sampling, is a process where the number of samples in the digitized signal is reduced by low-pass filtering and then removing samples from the digital stream. This process reduces the high frequency components and leaves predominantly the low frequency components in the sub-sampled signal.

To reduce the sampling rate of a digitized signal and still ensure accuracy of the resulting reduced-sample signal, there must be a relationship between the sampling rate of the digitized signal and the sub-sampling rate, herein referred to as the second frequency or $F_{max(low)}$. In particular, $F_{max(low)}$ must be rationally determinable from and lower than the value chosen for the sampling rate.

In the preferred form, the $F_{max(low)}$ value is determined from $F_{max(high)}$ through multiplication by a rational number. For example, 6,400 Hz may be obtained from 8000 Hz through multiplication by the rational number 4/5.

Therefore, once a value of $F_{max(high)}$ is chosen to sample the electrical vibration signal and create a digitized vibration signal, only frequencies that are rationally determinable from and lower than this frequency are available to sub-sample the digitized vibration signal.

In the above example, the list of available first frequencies, or $F_{max(high)}$, was noted as (in Hz): 40,000; 20,000; 10,000; 8,000; 5,000; 4,000; 2,500; 1,250; and 1,000. To accurately sub-sample signals that have been digitized using any of these frequencies, the second frequency, or $F_{max(low)}$, must be rationally determinable from and lower than the selected first frequency. The available $F_{max(low)}$ values are thus (in Hz): 20,000; 10,000; 8,000; 6,400; 5,000; 4,000; 3,200; 2,500; 2,000; 1,600; 1,250; 1,000; 800; 640; 500; 400; 320; 250; 200; 160; 125; 100; 80; 64; 50; 40; 20; and 10. These values are available for selection in step 29.

It will be appreciated that, although definite and precise values are provided herein, the devices used to implement the present invention may include inherent inaccuracies. For instance it is well known in the art that an ideal filter, which theoretically removes all frequencies below/over a specific frequency, is impossible to create. Therefore, when the values of frequency selection, filtering, and the like are specified herein, the values include deviations and approximations.

Once sub-sampled in step 28 based on the frequency selection in step 29, the resultant digital signal is sent to a waveform buffer in step 30. As described earlier, this buffer allows the accumulation of discrete digital vibration data. Once the buffer is full, the waveform is outputted as the second type of vibration signal, shown as step 32. Given that the digitized vibration signal has been sub-sampled using a frequency lower than the sampling frequency, the second type of vibration signal outputted is a low frequency waveform.

As described earlier, an equivalent frequency spectrum can be obtained by windowing and performing, for example, a Fast Fourier Transform (FFT) on the contents of the waveform buffer. This is shown in step 34. Once this is done, the average spectrum is calculated in step 36, and the frequency spectrum of the low frequency waveform is outputted in step 38.

The present invention is also advantageous where a demodulation procedure is to be performed on the digitized vibration signal. As used herein, the term demodulation encompasses processes substantially similar to demodulation such as techniques utilizing enveloping, high frequency enveloping, Spike Energy™ and PeakVue™. Other processes that are readily known to persons skilled in the art to achieve the same purpose as hereinafter described are also encompassed.

Demodulation is used to account for situations where certain machine problems remain hidden in a normal vibration reading, preventing early corrective action. Usually, these situations arise when the vibration is associated with an impact or impulse event. These events have a high frequency and a short duration. Unfortunately, when taking vibration readings, these vibration events are overwhelmed by the prominent long-duration and low frequency vibrations. An analogous example is where the impulse event is the striking of a gong (e.g., once per second or 1 Hz); while the long duration vibrations are the resulting sounds of a gong (e.g., 300 Hz). Here, the strike rate of 1 Hz modulates the carrier signal of 300 Hz. Therefore, by inspecting the variation in the amplitude of the 300 Hz carrier signal, one can determine or demodulate the strike rate.

In use, demodulation first removes the low-frequency components of the vibration signals using a high-pass filter at a frequency called $D_{min}$. $D_{min}$ is the corner demodulation frequency, below which frequencies are essentially filtered out, leaving only frequencies higher than $D_{min}$. To make the impulse events more prominent and easily identified later, the high-pass filtered signal is then envelope-detected. This envelope-detected signal is then processed as if it were an independent detected vibration signal.

In the present invention, $D_{min}$ is the third selectable frequency. Since the process of filtering at $D_{min}$ is much like the decimation at $F_{max(low)}$, the relationship between $D_{min}$ and the first frequency, $F_{max(high)}$, must be similar to the earlier-described relationship of $F_{max(low)}$ and $F_{max(high)}$. Specifically, $D_{min}$ must be rationally determinable from and lower than the value of $F_{max(high)}$. This relationship is necessary to digitally remove low frequency components from the digitized vibration signal accurately.

As with the selection of $F_{max(low)}$, the third frequency or $D_{min}$ values available for selection are equivalent to values rationally determined from and lower than the available $F_{max(high)}$ values. Where the available $F_{max(high)}$ values are (in Hz): 40,000; 20,000; 10,000; 8,000; 5,000; 4,000; 2,500; 1,250 and 1,000; the $D_{min}$ options are (in Hz): 20,000; 10,000; 8,000; 6,400; 5,000; 4,000; 3,200; 2,500; 2,000; 1,600; 1,250; 1,000; 800; 640; 500; 400; 320; 250; 200; 160; 125; 100; 80; 64; 50; 40; 20; and 10.

However, for practical results, the $D_{min}$ options may be limited to be at least one-tenth of the $F_{max(high)}$ value. With reference to the above list, the limited $D_{min}$ options are (in Hz): 20,000; 10,000; 8,000; 6,400; 5,000; 4,000; 3,200; 2,500; 2,000; 1,600; 1,250; 1,000; 800; 640; 500; 400; 320; 250; 200; 160; 125; and 100. Limiting the $D_{min}$ options is preferable because it limits the amount of low frequency noise in the signal, which would otherwise mask the modulation effect.

Once the selection of the first frequency or $F_{max(high)}$ is made, selection for the third frequency or $D_{min}$ is presented in step 40. As described above, the selection of frequency here governs the corner frequency at which the digitized vibration signal will be high-pass filtered. Once the value of $D_{min}$ is selected, the digitized vibration signal is high-pass filtered in step 41.

Once the low frequency components of the digitized vibration signal have been removed in step 41, the filtered vibration signal is envelope-detected in step 42. One simple method to detect the envelope of a signal is to rectify the signal (that is, high-pass filtered so low frequencies and the DC component have been removed, leaving the signal zero-centered). Alternative, peak-value detectors whose decay rate is appropriately chosen could be used. Persons skilled in the art will appreciate the plurality of other ways in which the envelope-detection could be carried out.

Following envelope detection, the vibration signal is sent to a decimation or sub-sampling filter in step 44. This filter works in the same manner as the decimation or sub-sampling filter described for step 28. The sub-sampling rate of this filter is chosen from the plurality of values that are rationally determinable from and lower than the first frequency, $F_{max(high)}$. In one preferred form, the sub-sampling rate for this decimation filter is the same as that chosen for the sub-sampling filter in step 28, which is the second frequency or $F_{max(low)}$.

The decimation filter in step 44 effectively extracts the frequencies of interest from the envelope-detected signal for analysis. Referring to the previously described analogy, the frequencies of interest would be around 1 Hz, which is the strike rate of the gong.

The decimation step 44 is not necessary in cases where the envelope detection step 42 has effectively sub-sampled or decimated the signal. That is, where steps 42 and 44 can be combined in a single step, it is not necessary to provide separate steps for each of steps 42 and 44.

The output of the decimation filter, or the envelope-filter if the envelope detection has resulted in a decimated signal, is then fed into a waveform buffer in step 46. As with the previous examples, the buffer accumulates the discrete digital signals to be outputted as a time waveform in step 48. The waveform of step 48 is the third type of vibration signal determinable using the present invention. In particular, the third type of signal is a demodulated time waveform.

In common with the processes for the first and second type of vibration signal, the third type of vibration signal can be expressed as a frequency spectrum through windowing and transformation, for example, under a Fast Fourier Transform (FFT) followed by averaging the spectrum, as shown in steps 50 and 52 respectively. The resulting frequency spectrum, which represents the demodulation spectrum, is outputted in step 54.

Where an accelerometer is used as a vibration sensor, the electrical vibration signals that are created by the accelerometer are representative of the acceleration of the vibrations sensed. Acceleration is one category of the sensed signal that is commonly analyzed. For comprehensive analysis, there is a need to also view and analyze other signal categories, such as velocity and displacement of the vibrations sensed.

In FIG. 1, the preferred form of the method of the present invention includes a selection by a user of a signal category in step 56. If acceleration is chosen as the category to analyze, the digitized signal is simply forwarded to the processing steps as previously described. No pre-processing is required here since the digitized vibration signal already represents the acceleration of the vibrations sensed.

Where velocity is chosen as the category of interest in step 56, the digitized vibration signal is pre-processed in step 58. The essential pre-processing is the integration of the acceleration-based digitized vibration signal. As is known in the art, integration of an acceleration-based signal will yield a velocity-based signal. Once this velocity-based signal is produced, it undergoes the processing steps as previously described to derive the different types of vibration signals.

Where displacement is chosen as the category of interest in step 56, the digitized vibration signal is pre-processed in both steps 58 and 60. As is known in the art, to obtain a displacement-based signal from an acceleration-based signal, double integration is necessary. Therefore, one integration process is carried out in step 58 as described above and a further integration process is carried out in step 60. This integration is carried out in series, such that the output of integration in step 58 is the input of the integration in step 60. Once the digitized vibration signal has undergone the double integration process, the resulting displacement-based vibration signal is sent for processing in the manner previously described.

It is preferable to have signal conditioning operations within the pre-processing of steps 58 and 60. For example, the DC component of the digitized vibration signal should be removed prior to integration to avoid unnecessary drift of the output. Once integrated, the resulting vibration signal should be scaled accordingly.

The apparatus of the invention will consist, in one embodiment, of known components performing the task involved in each step of FIG. 1. For example, persons skilled in the art will be familiar with variable rate analog-to-digital converters that could be employed to carry out step 14.

Depending on the application, the apparatus of the invention could be either a permanently installed monitoring equipment or a portable one. The apparatus will ideally include all processing components that are required to carry out the steps of FIG. 1. The outputs, which are the time waveforms and frequency spectrums from steps 20, 26, 32, 38, 48 and 54, can be either saved in a storage device within the apparatus of the invention or displayed on a display connectable to the apparatus.

In one embodiment, the display forms part of the apparatus so that the maintenance operator measuring the vibrations of a machine can immediately and conveniently view the multiple-type derived signals. In another embodiment, the apparatus is connectable to a computing device having a display. Examples of the computing device include personal computers, permanently installed computers, Personal Digital Assistants (PDAs) and portable computers.

The foregoing describes the invention including preferred forms thereof. Alterations and modifications as will be obvious to those skilled in the art are intended to be incorporated within the scope hereof, as defined by the accompanying claims.

What is claimed is:

1. A vibration analysis method producing multiple types of vibration signals from one vibration signal measured from an object, the method comprising the steps of:
   producing a single electrical vibration signal from vibrations of the object;
   selecting a first frequency from a set of frequency values;
   digitizing the single electrical vibration signal at the first frequency to produce a first digitized vibration signal;
   processing the first digitized vibration signal to produce a first representation of the electrical vibration signal;
   pre-processing the first digitized vibration signal based on a selected signal category;
   selecting a second frequency from a set of frequency values rationally determined from and lower than the first frequency;
   sub-sampling the pre-processed first digitized vibration signal at the second frequency to produce a second digitized vibration signal; and
   processing, using a processor, the second digitized vibration signal to produce a second type of vibration signal.

2. The vibration analysis method of claim 1 wherein said step of sub-sampling the first digitized vibration signal comprises the step of reducing the frequency of the second digital vibration signal to at least approximately the second frequency using at least one decimation filter.

3. The vibration analysis method of claim 1 wherein the first frequency is an upper cut-off frequency, the second frequency is a lower cut-off frequency, and the second digitized signal predominantly comprises the low frequency components from the first digital vibration signal, the step of processing the first digitized vibration signal further comprising the steps of:
buffering the digitized vibration signal as a first buffered signal;
producing a high frequency waveform of the digitized vibration signal from the first buffered signal; and
the step of processing the second digitized vibration further comprising the steps of:
buffering the second digitized vibration signal as a second buffered signal;
producing a low frequency waveform of the digitized vibration signal from the second buffered signal.

4. The method of claim 1 further comprising the steps of:
selecting a third frequency from a set of frequency values rationally determined from and lower than the first frequency;
filtering the digitized vibration signal to remove frequencies below the third frequency to produce a filtered vibration signal;
processing the filtered vibration signal to produce a third digitized vibration signal;
buffering the third digitized vibration signal as a third buffered signal;
producing a demodulation waveform of the digitized vibration signal from the third buffered signal.

5. The method of claim 4 further comprising the steps of:
selecting one of the first buffered signal, the second buffered signal, and the third buffered signal as a selected signal for processing;
windowing the selected signal to produce a windowed signal; and
transforming the windowed signal into a frequency spectrum.

6. The method of claim 5 further comprising the steps of:
repeating the steps of windowing and transforming to produce a selected number of frequency spectra from the selected signal; and
averaging the selected number of frequency spectra to produce an averaged frequency spectrum for the selected signal.

7. The method of claim 4 wherein said step of processing the filtered vibration signal further comprises the step of detecting the envelope of the third digitized vibration signal containing the frequencies of interest.

8. The method of claim 4 wherein said step of processing the filtered vibration signal further comprises the steps of:
detecting the envelope of the third digitized vibration signal to produce an envelope signal; and
reducing the number of samples in the envelope signal to the number of samples specified by a fourth frequency rationally determined from and lower than the first frequency to produce the third digitized vibration signal containing the frequencies of interest.

9. The method of claim 8 wherein said fourth frequency is equal to said second frequency.

10. The method of claim 1 wherein the vibration sensor is an accelerometer and the first digitized vibration signal is an acceleration vibration signal, the step of pre-processing the first digitized vibration signal further comprises the step of:
selecting a signal category from the categories of acceleration, velocity and displacement;
pre-processing the first digitized signal by integrating the acceleration vibration signal to obtain a velocity vibration signal when the selected signal category is velocity; and
pre-processing the first digitized signal by double-integrating the acceleration vibration signal to obtain a displacement vibration signal when the selected signal category is displacement.

11. A vibration analysis apparatus producing multiple types of vibration signals from one vibration signal measured from an object, the vibration analysis apparatus comprising:
a vibration transducer converting mechanical vibrations produced by an object into an electrical vibration signal;
an analog-to-digital converter digitizing the electrical vibration signal at a sampling rate corresponding to a first frequency selected from a set of frequency values into a digital vibration signal; and
a signal processor producing a first type of vibration signal from the digital vibration signal, pre-processing the digital vibration signal based on a selected signal category, sub-sampling the pre-processed digital vibration signal at a second frequency rationally determined from and lower than the first frequency to produce a second digital vibration signal containing a subset of vibration components contained in the electrical vibration signal, and producing a second type of vibration signal from the second digital vibration signal.

12. The apparatus of claim 11 wherein the first frequency is an upper cut-off frequency and the first set of components, the second frequency is a lower cut-off frequency, and the subset of vibration components predominantly includes the low frequency components from the digital vibration signal, said apparatus further comprising:
a first buffer for buffering the digitized vibration signal to produce a high frequency waveform of the digitized vibration signal; and
a second buffer for buffering the second digitized vibration signal to produce a low frequency waveform of the digitized vibration signal.

13. The apparatus of claim 11 wherein the signal processor filters the digital vibration signal at a third frequency rationally determined from and lower than the first frequency to produce a filtered vibration signal, processes the filtered vibration signal to produce a third digitized vibration signal, and produces a demodulation waveform representation of the single electrical vibration signal from the third digital vibration signal.

14. The apparatus of claim 13 wherein the signal processor processes the filtered vibration signal by detecting the envelope of the third digitized vibration signal.

15. The apparatus of claim 13 wherein the signal processor processes the filtered vibration signal by detecting the envelope of the third digitized vibration signal to produce an envelope signal, reduces the number of samples in the envelope signal to the number of samples specified by a fourth frequency rationally determined from and lower than the first frequency to produce the third digitized vibration signal containing the frequencies of interest.

16. The apparatus of claim 13 wherein the third frequency is demodulation frequency, the apparatus further comprising:
a third buffer for buffering the third digitized vibration signal to produce a demodulation waveform of the digitized vibration signal.

17. The apparatus of claim 16 wherein the signal processor operates on a selected one of the first buffer, the second buffer, and the third buffer, windows the contents of the selected buffer to produced a windowed signal and transforms the windowed signal to obtain a frequency spectrum of the digitized vibration signal corresponding to the selected buffer.

18. The apparatus of claim 17 wherein the signal processor collects multiple frequency spectra from the selected buffer and averages the collected frequency spectra to produce an averaged frequency spectrum.

19. A vibration analysis method producing multiple types of vibration signals from one vibration signal measured from an object, the method comprising the steps of:
producing a single electrical vibration signal from vibrations of the object;
selecting a first frequency from a set of frequency values;
digitizing the single electrical vibration signal at the first frequency to produce a first digitized vibration signal;
processing the first digitized vibration signal to produce a first representation of the electrical vibration signal;
selecting a second frequency from a set of frequency values rationally determined from and lower than the first frequency;
sub-sampling the first digitized vibration signal at the second frequency to produce a second digitized vibration signal;
processing the second digitized vibration signal to produce a second type of vibration signal;
selecting a third frequency from a set of frequency values rationally determined from and lower than the first frequency;
filtering the digitized vibration signal to remove frequencies below the third frequency to produce a filtered vibration signal;
processing, using a processor, the filtered vibration signal to produce a third digitized vibration signal, wherein the envelope of the filtered vibration signal is detected to produce an envelope signal, and the number of samples in the envelope signal is reduced to the number of samples specified by a fourth frequency rationally determined from and lower than the first frequency to produce the third digitized vibration signal; and
buffering the third digitized vibration signal as a third buffered signal.

20. A vibration analysis apparatus producing multiple types of vibration signals from one vibration signal measured from an object, the vibration analysis apparatus comprising:
a vibration transducer converting mechanical vibrations produced by an object into an electrical vibration signal;
an analog-to-digital converter digitizing the electrical vibration signal at a sampling rate corresponding to a first frequency selected from a set of frequency values into a digital vibration signal; and
a signal processor producing a first type of vibration signal from the digital vibration signal, sampling the digital vibration signal at a second frequency rationally determined from and lower than the first frequency to produce a second digital vibration signal containing a subset of vibration components contained in the electrical vibration signal, and producing a second type of vibration signal from the second digital vibration signal;
wherein the signal processor high-pass filters the digital vibration signal at a third frequency rationally determined from and lower than the first frequency to produce a filtered vibration signal, processes the filtered vibration signal by envelope detection to produce an envelope signal, and reduces the number of samples in the envelope signal to the number of samples specified by a fourth frequency rationally determined from and lower than the first frequency to produce the third digitized vibration signal.

* * * * *